(12) United States Patent
Van Der Zaag et al.

(10) Patent No.: US 10,281,453 B2
(45) Date of Patent: May 7, 2019

(54) APPARATUS FOR THE PROCESSING OF SINGLE MOLECULES

(71) Applicant: KONINKLIJKE PHILIPS N.V., Eindhoven (NL)

(72) Inventors: Pieter Jan Van Der Zaag, Waalre (NL); Reinder Coehoorn, Eindhoven (NL); Falco Cornelius Marinus Jacobus Maria Van Delft, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 36 days.

(21) Appl. No.: 14/345,261

(22) PCT Filed: Sep. 25, 2012

(86) PCT No.: PCT/IB2012/055091
§ 371 (c)(1),
(2) Date: Mar. 17, 2014

(87) PCT Pub. No.: WO2013/046116
PCT Pub. Date: Apr. 4, 2013

(65) Prior Publication Data
US 2014/0349892 A1   Nov. 27, 2014

Related U.S. Application Data

(60) Provisional application No. 61/540,014, filed on Sep. 28, 2011.

(30) Foreign Application Priority Data

Dec. 5, 2011 (EP) ..................................... 11191966

(51) Int. Cl.
*G01N 33/487* (2006.01)

(52) U.S. Cl.
CPC .............................. *G01N 33/48721* (2013.01)

(58) Field of Classification Search
CPC ................................................ G01N 33/48721
See application file for complete search history.

(56) References Cited

U.S. PATENT DOCUMENTS 6,503,409 B1 * 1/2003 Fleming .......................... 216/56
7,468,271 B2   12/2008 Golovchenko et al.
(Continued)

FOREIGN PATENT DOCUMENTS

JP   H08315760 A   11/1996
JP   H1131655 A    2/1999
(Continued)

OTHER PUBLICATIONS

Garaj, Slaven, et al. "Graphene as a subnanometre trans-electrode membrane." Nature 467.7312 (2010): 190-193.*
(Continued)

*Primary Examiner* — Robert J Eom

(57) ABSTRACT

The invention relates to an apparatus (100) and a method for the processing of single molecules, particularly for the sensing or sequencing of single-stranded DNA. A bottom layer (110) and an electrically conductive top layer (120) with a first and a second slit (111,121), respectively, are disposed on top of each other such that an aperture (A) is formed by the slits. The slits (111,121) are preferably perpendicular to each other. An electrical circuit (140) may be connected to the top layer (120), allowing to sense single molecules that pass through the aperture (A).

19 Claims, 5 Drawing Sheets

(56) References Cited

U.S. PATENT DOCUMENTS

| | | | |
|---|---|---|---|
| 7,582,490 | B2 | 9/2009 | Golovchenko et al. |
| 7,678,562 | B2 * | 3/2010 | Ling .................... 435/283.1 |
| 8,486,630 | B2 | 7/2013 | Pan et al. |
| 2004/0229386 | A1 | 11/2004 | Golovchenko et al. |
| 2010/0327847 | A1 | 12/2010 | Leiber et al. |
| 2012/0037919 | A1 | 2/2012 | Xu et al. |
| 2012/0234679 | A1 | 9/2012 | Garaj et al. |
| 2012/0264632 | A1 | 10/2012 | Leamon et al. |
| 2014/0349892 | A1 | 11/2014 | Van Der Zaag |

FOREIGN PATENT DOCUMENTS

| | | | |
|---|---|---|---|
| JP | 2002522780 | A | 7/2002 |
| JP | 2003533676 | A | 11/2003 |
| JP | 2008536124 | A | 9/2008 |
| JP | 2010540263 | A | 12/2010 |
| JP | 2011046706 | A | 3/2011 |
| WO | WO2009035647 | | 3/2009 |
| WO | WO2011046706 | | 4/2011 |
| WO | WO2011047582 | | 4/2011 |
| WO | WO 2010/042514 A1 * | | 4/2014 |

OTHER PUBLICATIONS

H.W.CH. Postma, "Rapid Sequencing of Individual DNA Molecules in Graphene Nanogaps", Nano Lett. 2010, 10, pp. 420-425.

Novoselov. K.S. et al., "Electric Field effect in Atomically thin carbon films", American Association for the Advancement of Science, vol. 306, Nr: 5696, pp. 666-669.

Lifshitz, N. et al., "Enhanced channel mobility in Polysilicon Thin Film Transistors", IEEE Electron Device Letters, vol. 15, No. 8, Aug. 1994.

* cited by examiner

APPARATUS FOR THE PROCESSING OF SINGLE MOLECULES

CROSS-REFERENCE TO PRIOR APPLICATIONS

This application is the U.S. National Phase application under 35 U.S.C. § 371 of International Application Serial No. PCT/IB2012/055091, filed on Sep. 25, 2012, which claims the benefit of European Application Serial No. 11191966.8, filed Dec. 5, 2011, and U.S. Application Ser. No. 61/540,014, filed on Sep. 28, 2011. These applications are hereby incorporated by reference herein.

FIELD OF THE INVENTION

The invention relates to an apparatus and a method for the processing of single molecules. Moreover, it relates to a method for manufacturing such an apparatus.

BACKGROUND OF THE INVENTION

The U.S. 2010/0327847 A1 discloses a solid state molecular sensor having an aperture extending through a graphene layer. A change in an electrical characteristic of said layer is measured when a molecule passes through said aperture. One drawback of this sensor is the high electrical conductivity of the graphene layer, compared to which conductivity changes induced by a molecule are very small.

Furthermore, it has been described in literature (H. W. Ch. Postma, "Rapid sequencing of individual DNA molecules in graphene nanogaps", Nano Lett. 10 (2010) 420-425) that a DNA molecule can be sequenced by passing it through a gap between two graphene layers. The associated apparatus is, however, mechanically not very robust as free graphene layers are used. Moreover, the comparatively long gap between said layers allows long molecules to pass it with many different orientations and configurations, making the interpretation of measurement results difficult.

SUMMARY OF THE INVENTION

It is an object of the invention to provide improved means for the processing of single molecules, particularly for the sequencing of nucleic acids like DNA.

This object is achieved by an apparatus according to claims 1 and 2, and by a method according to claims 3 and 4. Preferred embodiments are disclosed in the dependent claims.

An apparatus according to the present invention serves for the processing of single molecules (or atoms), particularly of macromolecules like proteins or nucleic acids. In this context, the term "nucleic acids" shall most generally comprise molecules (e.g. DNA, RNA) that contain naturally and/or non-naturally occurring nucleotides or modifications thereof as well as LNA (locked nucleic acids) and PNA (peptide nucleic acids). The "processing" of these molecules may comprise their physical and/or chemical transformation or alternation. In many important applications, the processing will however be a sensing, particularly serving for the detection of different sections of a molecule. Thus it may for example be possible to sequence ss-DNA. According to a first aspect of the invention, the apparatus comprises the following components:

a) A first layer of a first material, wherein the first layer comprises a first slit. For the purpose of reference, the first layer will in the following be called "bottom layer" (indicating its usual position in the drawings but without prejudice with respect to its orientation in reality). The term "slit" shall denote in the context of the present application a connected opening, gap, hole, or aperture of generally any shape, though it will often refer to an elongated (e.g. rectangular) slit in the narrower sense of the word.

b) A second layer that is disposed on the aforementioned bottom layer and that has a second slit. For the purpose of reference, this second layer will in the following be called "top layer". The second slit in the top layer shall at least partially overlap the first slit in the bottom layer such that both slits together constitute an aperture through which single molecules can pass. Moreover, the top layer shall (at least in part) be electrically conductive.

According to a second aspect of the invention, the apparatus comprises an electrically conductive layer that provides an aperture through which single molecules can pass and that has an electrical insulation on at least a part of its surface. Said conductive layer will be called "top layer" in the following because it can be identified with the conductive top layer of the aforementioned embodiment. In fact, the apparatus according to the second aspect of the invention can be considered as an apparatus according to the first aspect in which the bottom layer provides the insulation. It should be noted that the insulation will typically be absent at and/or within the aperture.

The invention further relates to a method for the production of an apparatus of the kind described above, said method comprising the following steps which can be executed in the listed or any other appropriate order:

a) Providing a bottom layer with a first slit. The bottom layer may for example be first provided as a homogeneous layer of material, into which a slit is then fabricated by methods like lithography.

b) Depositing an electrically conductive top layer on said bottom layer.

c) Producing a second slit in the top layer, wherein this second slit is disposed above the first slit such that both slits together yield an aperture.

Moreover, the invention relates to a method for the processing of single molecules, said method comprising the following steps:

a) Letting a molecule sequentially pass through a second slit in an electrically conductive top layer and a first slit in an adjacent bottom layer, wherein said slits commonly provide an aperture. The passing of the molecule can be actively induced or assisted, for example with appropriate electrical, magnetic, or hydrodynamic forces. It is however also possible that the molecules just passively migrate through the aperture, driven solely by their random (thermal) movement. It should be noted that both directions of passage shall be comprised by this step, i.e. passing first through the top and then through the bottom layer or vice versa.

c) Executing or sensing an interaction between the aforementioned molecule and the top layer and/or the bottom layer where the molecule passes through said aperture.

The apparatus and the methods described above are different realizations of a common concept, i.e. the provision of an aperture in a conductive layer that is (functionally) supported or supplemented by an additional component (the bottom layer and/or the insulation), wherein the aperture may be formed by appropriately arranged slits in a top and a bottom layer. Explanations and definitions provided for one of these realizations are therefore analogously valid for the other realizations, too.

The apparatus and the methods have the advantage that the mechanical and/or electrical properties of a conductive layer can favorably be adjusted by an additional component, i.e. the bottom layer and/or the insulation. Moreover, an aperture is provided with adjustable shape and dimension through which single molecules can pass. Particularly if an aperture with a comparatively compact (e.g. circular or square) shape is used, long molecules like ss-DNA will be able to pass through the aperture only in axial direction, thus providing well defined conditions for their processing. At the same time, the aperture can readily be produced as it basically consists of two slits. Finally, it is an advantage that the electrically conductive top layer can be completely divided into two separate parts (separated by the second slit) such that no background current will flow when the second slit is empty. Additionally, background current can be suppressed by the insulation of the conductive top layer.

In the following, various preferred embodiments of the invention will be described that relate both to the apparatus and the methods described above.

The first slit in the bottom layer and the second slit in the top layer are arranged one above the other such that they commonly yield the desired aperture. In general, it is possible that one slit is completely overlapped by the other (e.g. if both slits are identical in size and shape and exactly aligned). The resulting aperture would then correspond in size and shape to this (smaller) slit. Though such an embodiment shall be comprised by the invention, it is preferred that the first slit and the second slit do not completely overlap. The aperture, which always corresponds to the region of overlap between the slits, will then be smaller than each of the slits alone. This design is favorable in that a small aperture can be more easily produced with the help of comparatively large apertures (the slits).

The first and the second slit may have elongated (e.g. rectangular) shapes that are oriented coaxially with a relative shift in axial direction. Hence, only a smaller area where these slits overlap will constitute the aperture. Most preferably, the two slits are however oriented oblique with respect to each other, particularly perpendicular. In this case the exact relative position of the slits can largely vary, allowing for large production tolerances, without affecting the size and shape of the resulting aperture.

The first and/or the second slit may be completely surrounded by the corresponding layer (being an interior opening of said layer), it may have a connection to one border of the layer, or it may cut the layer into two disconnected parts. The latter case may preferably be realized for the top layer and the second slit. The two parts of the top layer are then electrically disconnected, yielding zero background currents across the second slit. Most preferably, this is combined with a first slit that lies completely in the interior of its layer and thus provides a mechanically stable, one-piece bottom layer.

The top layer is optionally provided with an electrical insulation on at least a part of its surface, preferably on its whole surface besides at the aperture and/or the second slit. The electrical insulation prevents the flow of undesired electrical currents, particularly currents between two disconnected parts of the top layer that are separated by the second slit (cf. aforementioned embodiment). Thus only currents through a region of interest are generated (i.e. typically currents across the second slit), while currents through the surrounding sample medium and/or through other components of the apparatus (e.g. the bottom layer) are prevented or at least minimized.

The electrically conductive top layer may preferably comprise graphene. Graphene is a preferred material due to its favorable electrical and mechanical properties at nanoscale dimensions.

The thickness of the top layer (determined in the region of the second slit) is preferably less than about 2 nm, most preferably less than about 1 nm. If interactions with molecules within the second slit shall be measured, low thicknesses are advantageous because they yield a higher spatial resolution. Thus single bases of a DNA strand can for instance be detected by a tunnel current through them, said bases typically having a distance of about 0.3 nm from each other.

In case of a top layer that comprises or consists of graphene, said graphene may be present in five monolayers or less, preferably two mono layers, or more preferably in a single monolayer. Thus the aforementioned favorable low thickness can be achieved.

According to another embodiment of the invention, an additional layer may be disposed on the top layer, said additional layer leaving the second slit open. The additional layer may particularly be electrically non-conductive. An additional layer may be advantageous in that it increases the mechanical stability, provides an electrical insulation (if it is non-conductive), and helps to orient molecules appropriately.

The top layer and/or the bottom layer and/or the additional layer may preferably have a thickness between about 10 nm and about 1000 nm. This thickness is considerably larger than the diameter of typical elongated molecules to be processed, for example of ss-DNA. Such molecules will therefore be orientated in the plane defined by the slit in the corresponding layer, which further contributes to a definite orientation of the molecules during their passage through the aperture.

In general, the top layer may consist of two or more sub-layers of different materials (several sub-layers of the same material, i.e. graphene, were already described above). At least one of these sub-layers should be electrically conductive to provide the electrical conductivity of the whole top layer. By combining different materials, the electrical and mechanical properties of the top layer can better and independently be adjusted.

In general, no restrictions are made with respect to the electrical properties of the bottom layer, which may hence for example comprise an electrical conductor or semiconductor. Most preferably, the bottom layer (or at least its interface to the top layer) is however electrically non-conductive. It may in particular comprise a dielectric material, for example silicon dioxide ($SiO_2$) and/or silicon nitride ($SiN_x$). These materials are suitable carriers or substrates on which microelectronic or micromechanical structures can be built with known manufacturing procedures. The bottom layer may be a uniform layer or comprised of sub-layers. As mentioned above, an electrically insulating layer should be disposed between the bottom layer (if it is a conductor or semiconductor) and the top layer in order to prevent the flow of undesired currents through the bottom layer.

The size and shape of the aperture formed by the first and the second slit will usually be chosen with respect to be intended application, particularly with respect to the molecules that shall be processed. Preferably, the size of the aperture ranges between about 0.1 $nm^2$ and 10 $nm^2$, most preferably between about 2 $nm^2$ and 5 $nm^2$. The associated shape of the aperture is preferably circular, rectangular, or square. The mentioned sizes are suited for the processing of for example ss-DNA.

The width of the first and/or the second slit preferably ranges between about 0.1 nm and about 100 nm. The length of the first and/or the second slit preferably ranges between about 0.1 µm and about 1 µm. Slits with the mentioned sizes can readily be produced with known procedures, while they allow the formation of apertures of appropriate (small) sizes.

Depending on the intended processing of the single molecules, additional components may be needed. Such components may particularly be realized by an electrical circuit adapted to control interactions between the top layer and molecules passing through the aperture. Such a circuit is preferably connected to the top layer. In addition, the aperture may be embedded in a micro fluidic circuit ensuring the transfer of the molecules of interest, e.g. DNA fragments, to the aperture.

In a preferred embodiment, the aforementioned circuit may be adapted to sense conductivity changes which occur when a molecule or different portions of a molecule pass through the aperture (and/or the second slit in the top layer). Thus it is for example possible to achieve the sequencing of ss-DNA by detecting the occurrence of a tunneling current across the second slit (which should be/is base dependent).

To allow for a parallel processing of a plurality of single molecules, it is preferred that a plurality of apertures is provided. Preferably, these apertures are provided on a common carrier or substrate, wherein each aperture is formed between a corresponding first slit in a bottom layer and a corresponding second slit in a top layer. The bottom layers and top layers corresponding to each aperture may be different for each aperture or may all be the same. Most preferably, a plurality of first slits is provided in a common bottom layer while the corresponding second slits are realized in separate top layers.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

The U.S. 2010/0327847 A1 describes the use of a graphene layer/electrode in nanopore sequencing. It is proposed in this patent that a nanopore is embedded in the graphene, leaving areas besides the nanopore.

However, it is already known that graphene has a very high conductivity. A mobility of around 10,000 $cm^2/Vs$ at room temperature has been reported (K. S. Novoselov, A. K. Geim, S. V. Morozov, D. Jiang, Y. Zhang, S. V. Dubonos, I. V. Grigorieva, and A. A. Firsov, "Electric Field Effect in Atomically Thin Carbon Films", Science, 306 (204) 666-669). Hence, the current in the device of the U.S. 2010/0327847 A1 will not or only hardly be modulated and the devices will have a poor effectiveness in determining the bases passing through the nanopore, as nearly all of the current will pass by the nanopore in the remaining graphene.

In view of this, it seems to be more effective to use nanogaps, as proposed by Postma (H. W. Ch. Postma, "Rapid sequencing of individual DNA molecules in graphene nanogaps", Nano Lett. 10 (2010) 420-425). As stated in this paper, using a nanogap has the additional advantage that problems of aligning the (nano)-electrodes to the nanopore are circumvented.

However, for practical purposes the device considered by Postma in his theoretical calculations has two important shortcomings:

To generate devices which can be easily manufactured the nanogaps or "slits" will have to have a finite length spanning the whole graphene electrode. This will be a dimension in the order of 0.1-1 µm. As single-stranded DNA (ss-DNA) to be measured is very flexible, this will allow DNA to pass through the nanogap in many ways, in particular folded. This will destroy the chance of measuring at the envisioned single-base resolution.

The graphene layers have no mechanical support and although graphene is a strong material the devices thus fabricated will not be very robust.

Shunt currents through the buffer liquid charged with ions will occur that may overwhelm any tunnel current to be measured.

To deal with these described issues it is proposed here not to use a nanohole neither a nanogap device but to use a different device: a crossed-slit (graphene) device.

Figure 1:
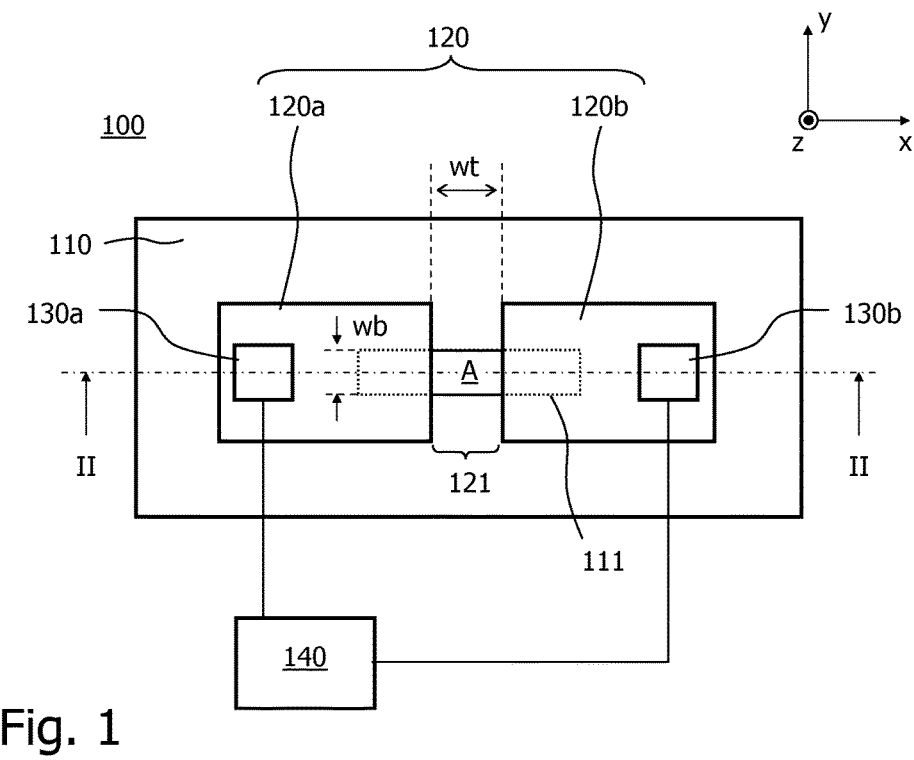
FIG. 1 shows a schematic top view onto an apparatus according to the present invention.
Figure 2:
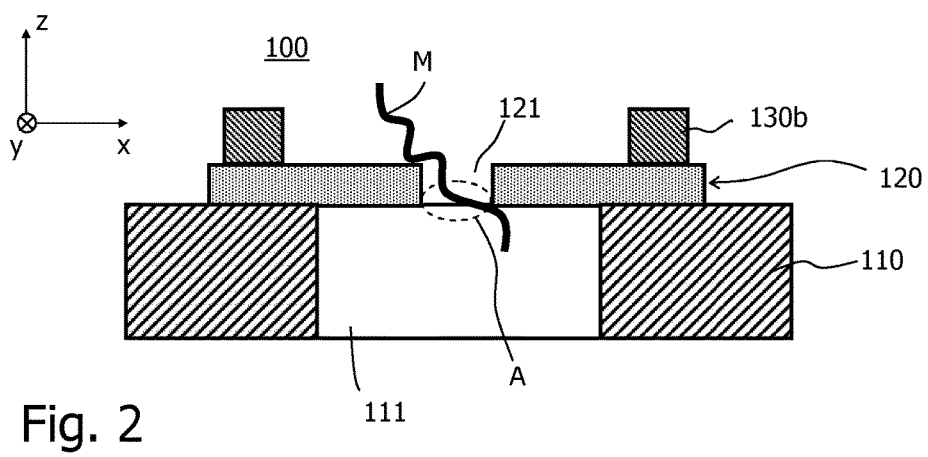
FIG. 2 shows a cross section through the apparatus along line II-II of FIG. 1.

FIGS. 1 and 2 schematically sketch an exemplary apparatus 100 that is designed according to the aforementioned concept. The central components of this apparatus 100 are two layers, namely:

A "bottom layer" 110 comprising an elongated, rectangular first slit 111 of width wb that extends in x-direction.

A "top layer" 120 that is disposed on the aforementioned bottom layer 110, said top layer consisting of two disconnected parts 120a and 120b which are separated by a second slit 121 of width wt that extends in y-direction.

The first slit 111 and the second slit 121 are oriented perpendicular with respect to each other and overlap partially in the region of a (square) aperture A through which single molecules M can pass.

As indicating in the Figures, the apparatus 100 further comprises contacts 130a and 130b disposed on the top layer parts 120a and 120b, respectively. Via these contacts, the top layer is connected to a circuit 140. This circuit 140 is adapted to sense electrical interactions that take place between the top layer 120 and single molecules passing through the aperture A.

The described crossed nano-slit device 100 has the following advantages over known devices to perform transverse-conductance based sequencing using graphene nanopores:

Contrary to the nanohole device structure proposed in the U.S. 2010/0327847 A1, a (tunneling) current will only be generated if and when DNA will pass through the nano-opening. Moreover this device has the crucial advantage of doing measurement against zero background, i.e. a (very) limited to no signal occurs when no DNA passes through the device.

This device structure can be manufactured easily and guarantee a single nano-opening through which ss-DNA can only pass. No nanohole has to be made, just two slits with nm width.

The ss-DNA cannot pass through this device in a folded manner, which would also preclude the detection of single bases.

FIGS. 3 to 12 illustrate consecutive steps of the production of an apparatus according to the present invention, wherein each Figure shows a sectional side view on the left and a top view on the right hand side.

Figure 3:
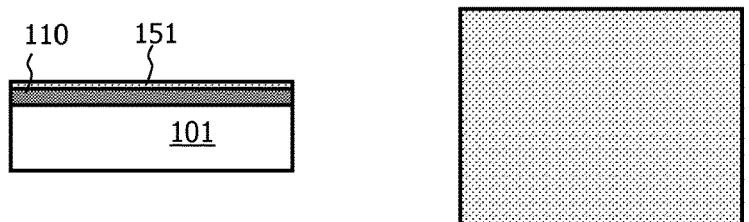
FIGS. 3-12 shown consecutive steps of the manufacturing of an apparatus according to the invention.

Starting with FIG. 3, a silicon (Si) substrate 101 is provided as a carrier, on which an (insulating) dielectric "bottom layer" 110 of $SiO_2$ has been deposited (with a typical thickness of about 100 nm). Furthermore, a resist layer 151 has been deposited on top of this (with a typical thickness of about 50 nm; the resist may for example be a high-resolution, positive E-beam resist like ZEP520 from Zeon Corp.).

Figure 4:
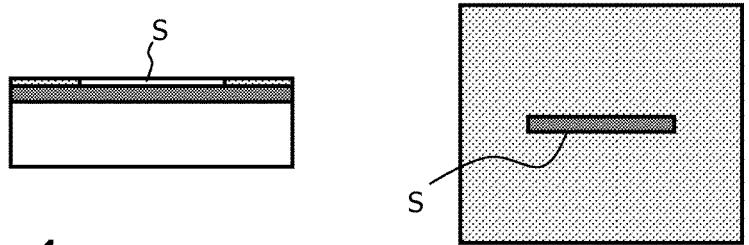

In FIG. 4, a slit S has been produced in the resist layer 151 by electron beam lithography (EBL) or extreme UV lithography.

Figure 5:
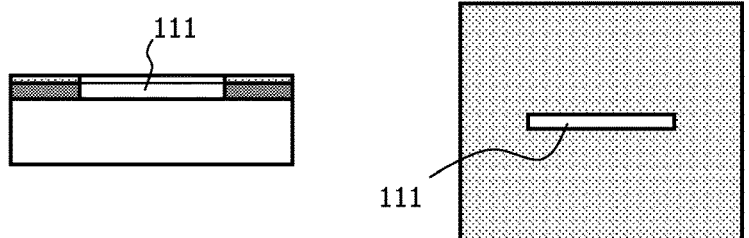

In FIG. 5, the second slit 111 has been produced in the bottom layer 110 by reactive ion etching (RIE) through the slit in the resist 151.

Figure 6:
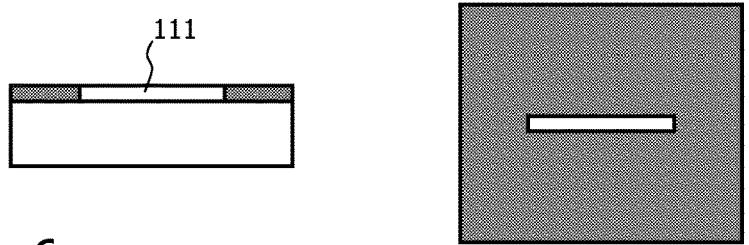
Figure 7:
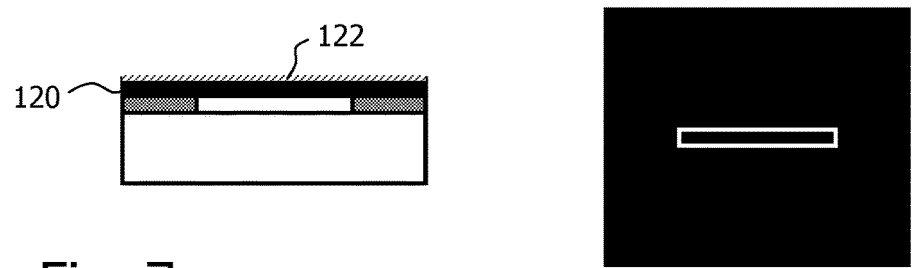

In FIG. 6, the resist 151 has been removed, and in FIG. 7 a graphene top layer 120 with a thickness of about 1 nm has been deposited on top of the bottom layer 110 by the addition of floating graphene. In case an insulating layer 122 is provided on top of the graphene layer 120, this isolator/insulator could be part of the package in the floating graphene added.

Figure 8:
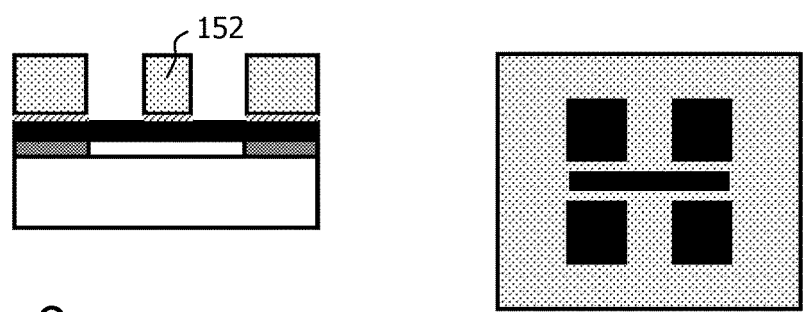

In FIG. 8, a resist 152 has been applied upon the graphene top layer 120, said resist being for example a layer of PMMA (poly-methylmethacrylate) of about 100 nm thickness. Moreover, this resist 152 has been structured by electron beam lithography to provide four holes H. In case an insulating layer 122 has been provided on top of the graphene layer 120, this insulator should be removed here by sputter etching, RIE or wet-chemically, in order to allow electrical contact between the subsequent (Cr) Au (layers 131 and 132) and the graphene. The use of other resists than PMMA, e.g. of ZEP520, is also possible, especially when they are removed in the lift-off step anyhow.

Figure 9:
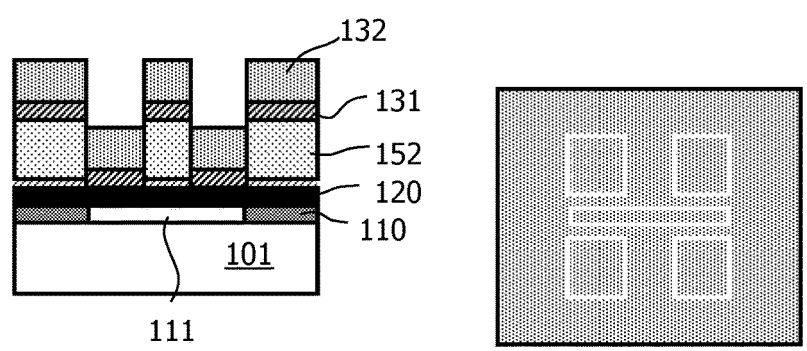

According to FIG. 9, a chromium (Cr) layer 131 (thickness about 5 nm) and a gold (Au) layer 132 (thickness about 100 nm) have been deposited on top of the device. The chromium layer can be omitted if gold sufficiently binds to the underlying layers.

Figure 10:
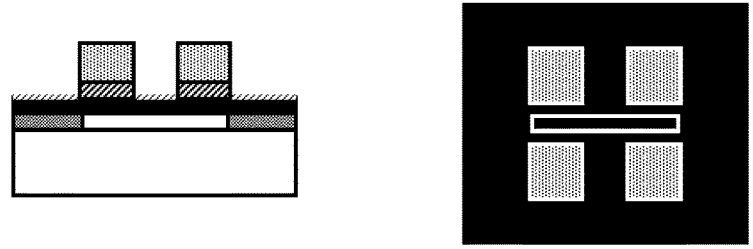

In FIG. 10, the resist 152 has been lifted off, leaving the Au/Cr only at the four holes where it is directly on top of the graphene 120.

Figure 11:
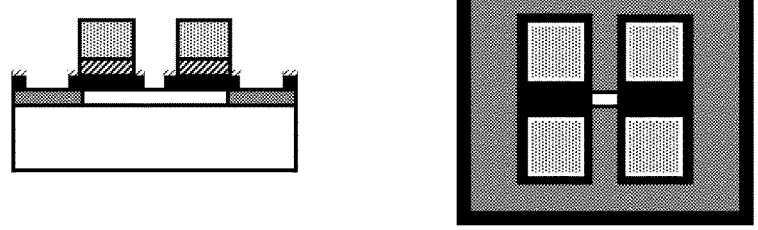

In FIG. 11, Focused Ion Beam (FIB) or high dose e-beam lithography (or other fine-line lithography) has been used to pattern the graphene top layer 110. While the bottom layer could be patterned with conventional lithography (yielding a resolution of around 5 nm), the patterning of the graphene top layer has to be done in a different technique as the gap between the graphene electrodes will have to be in the 1-2 nm range. This can be done by e-beam lithography using electrons of around 100 keV. As a result of the patterning, two disconnected parts 120a and 120b of graphene are produced, separated by the second slit. Moreover, a frame 120c of graphene is left along the border of the device.

Figure 12:
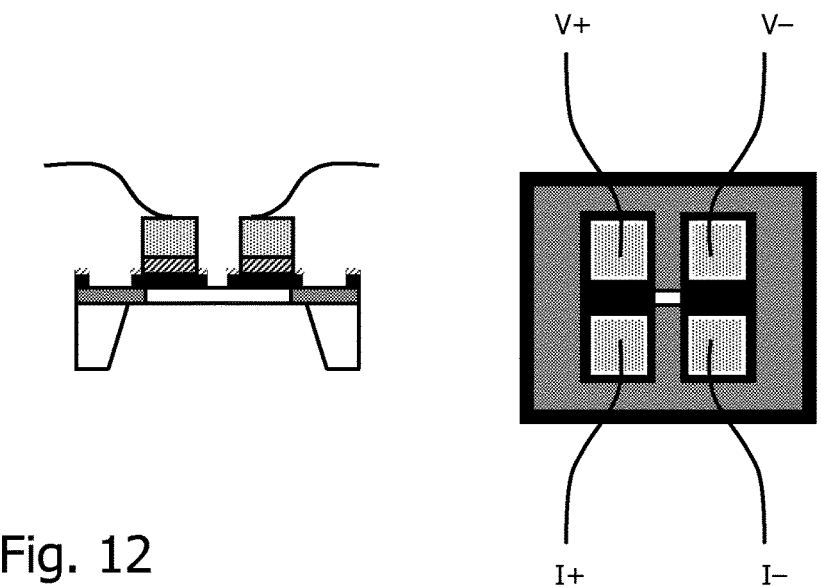

FIG. 12 illustrates the final step in which silicon of the silicon layer 101 has been removed from the backside, thus opening an aperture formed between the first and the second slit in the bottom and the top layer, respectively. Moreover, the Au/Cr contacts have been connected to a circuit (not shown) by which sensing in the aperture can be realized.

Alignment of the bottom and top layers with the nanoslits is relatively easy, as the length of each slit can be made sufficiently long (0.1-1 µm) so that achieving overlay will be a straight forward task even with conventional lithographic tools. This is a central aspect of the proposed approach, viz. that the problem of making a nanohole is replaced by making two slits which together provide the nano-opening.

As a further embodiment it is proposed that a protective layer on top of the graphene top layer is provided and given an optimal, for instance conical, shape. This increases the height of the second slit on top of the graphene and thereby decreases the angle under which ss-DNA will pass through the nano-opening in the crossed slit device.

Figure 13:
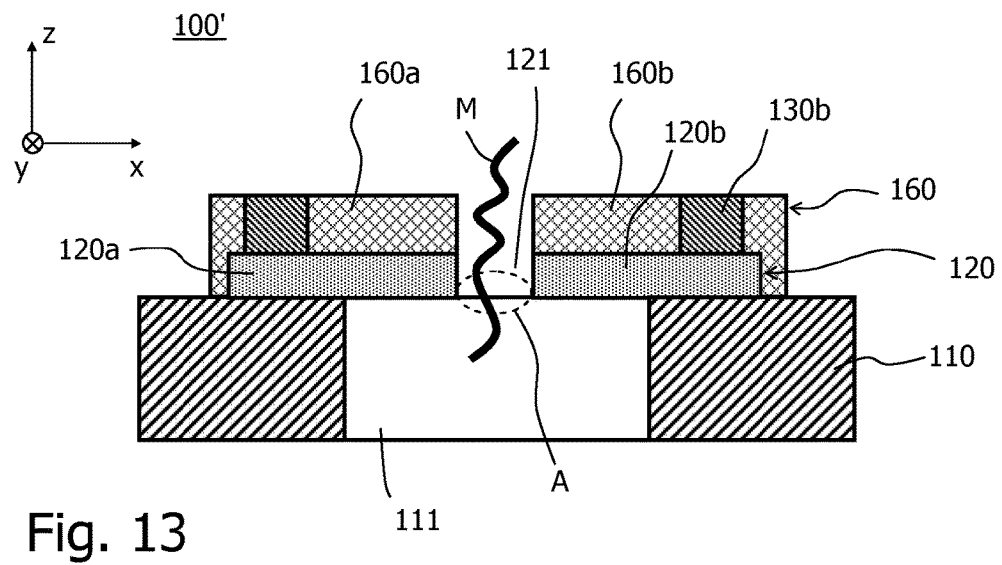
FIG. 13 shows a modification of the apparatus of FIGS. 1 and 2 in which an additional layer is provided on the top layer.

FIG. 13 illustrates this in a sectional view (like that of FIG. 2) of an apparatus 100' that is a modified version of the apparatus 100 described above. The (only) new component in this apparatus 100' is an electrically non-conductive "additional layer" 160 which is disposed on the top layer 120, leaving (only) the second slit 121 open. Accordingly, the additional layer 160 comprises two separate parts 160a and 160b.

The additional layer 160 electrically insulates the conductive top layer 120 from the surrounding sample medium, thus preventing the flow of shunt currents when a voltage is applied to the top layer. Moreover, the additional layer 160 adds to the thickness (in z-direction) of the second slit 121, which helps to orient molecules M appropriately before their passage through the aperture A.

Figure 14:
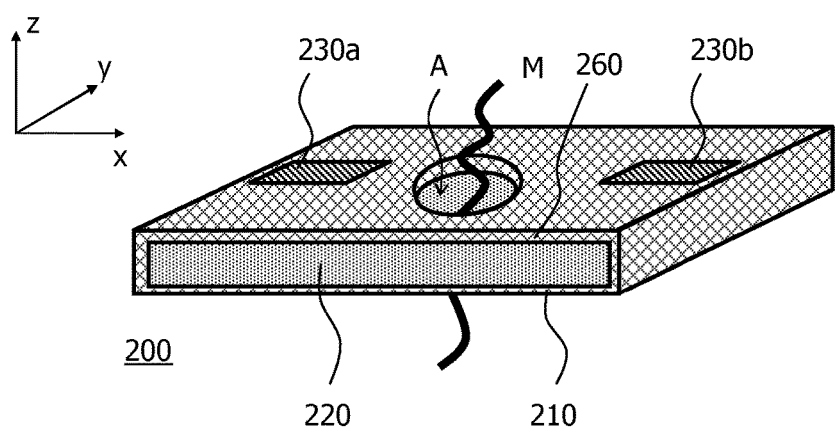
FIG. 14 shows an alternative apparatus in which an electrically conductive layer is encapsulated by an insulation.

FIG. 14 shows in a schematic perspective a section through an apparatus 200 according a second aspect of the invention. Components that are similar or identical to those of the previous embodiments are designated with reference signs increased by 100 and will not be described again. The apparatus 200 comprises the following components:

An electrically conductive "top layer" 220 with an aperture A through which single molecules M can pass. This top layer may particularly be a graphene (mono-, double- or multi-) layer.

An electrical insulation that covers the aforementioned top layer 220 (besides within the aperture A) and that consists of a "bottom layer" 210 and an "additional layer" 260.

Two electrical contacts 230a and 230b disposed on opposite sides of the aperture A and in electrical contact to the top layer 220. The contacts may be connected to an external circuit (not shown).

It should be noted that the terms "top layer", "bottom layer", and "additional layer" are primarily chosen to show the correspondence to the previous embodiments of the invention. In practice, the "bottom layer" and the "additional layer" may be constituted by a homogenous insulation.

The aperture A may be considered as being formed by an overlap between a "first slit" in the bottom layer 210 and a "second slit" in the top layer 220 (and a third slit in the additional layer 260). In the shown example, these slits are identical in shape and size, and the aperture A is approximately circular. It could however also have a shape as in the previous embodiments, particularly a shape that divides the conductive layer 220 in two disconnected parts.

The apparatus 200 has the advantage that, when a voltage is applied between the contacts 230a and 230b, no currents can flow through the sample medium besides within the aperture A. This reduces the contribution of undesirable background currents when measurements in the aperture A are intended.

It should be noted that the width of double-stranded DNA is 2.3 nm, hence that of ss-DNA will be around 1.1 nm, so the created nano-opening of 2 by 5 nm will be sufficiently small to pass one and at the most two ss-DNA strands. If the latter is the case this can be easily dealt with, as it is foreseen that the devices will be operated in a (massively) parallel fashion. Hence, the unfortunate chance that some devices will be fed multiple DNA strand at the same time can be dealt with by ignoring the data date coming from these cells/pixels of the total device.

The inventive nanopore aperture is preferably adapted to measure conductivity. Under measurement of conductivity changes is understood that this can be a dc current-voltage measurement, an ac current-voltage measurement, or an ac current-voltage measurement carried out by superimposing on a dc voltage a (small) ac voltage (a so-called admittance measurement), or in general a measurement of the current in response to any time-dependent applied voltage. Preferably an ac measurement is done at a measurement frequency which exceeds the typical type scale of any ionic moment in the buffer medium, so as to be not influence by ionic modulations in the buffer medium.

Moreover, it should be noted that the described technique can of course be used to process other molecules than ss-DNA, for example double-stranded DNA (ds-DNA), general nucleic acids, or proteins. In ds-DNA, the number of base pairs may for example be counted (with or without precisely determining their sequence). Alternatively epigenetic changes to the DNA may be determined. The approach of the invention can also be used to design an "electronic nose" for the detection of trace elements, molecules or molecular fragments, particularly elements, molecules or molecular fragments that can induce a tunnel current in the slit of a conductive (e.g. graphene) layer. In this latter application the elements and molecules to be detected may be in a gaseous or liquid medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An apparatus for the processing of single molecules, comprising:
a bottom layer with a first slit;
an electrically conductive top layer with a second slit that is disposed on the bottom layer, said second slit being disposed above the first slit to provide an aperture having a dimension through which single molecules can pass therethrough,
wherein the first slit is oriented oblique to the second slit;
said electrically conductive top layer comprising a material having a high electrical conductivity and further comprising an electrical insulation on at least a part of its surface;
wherein the electrically conductive top layer comprises graphene in less than five monolayers;
wherein the electrical insulation on at least a part of the surface of the electrically conductive top layer is an additional layer disposed on the electrically conductive top layer other than at the aperture;
wherein the additional layer covers a portion of edges of the top surface of the electrically conductive top layer at proximal sides of the aperture; and
wherein the electrically conductive top layer is configured to have a substantially in-line surface on an entire inside wall of the aperture.

2. The apparatus according to claim 1,
wherein the second slit divides the electrically conductive top layer into two disconnected parts.

3. The apparatus according to claim 1,
wherein the electrically conductive top layer and/or the bottom layer and/or the additional layer has a thickness between 10 nm and 1000 nm.

4. The apparatus according to claim 1,
wherein the bottom layer comprises a dielectric material.

5. The apparatus according to claim 4, wherein the bottom layer comprises silicon dioxide and/or silicon nitride.

6. The apparatus according to claim 1,
wherein the aperture has a size between 0.1 $nm^2$ and 10 $nm^2$.

7. The apparatus according to claim 1,
wherein the first slit and/or the second slit has a width between 0.1 nm and 100 nm.

8. The apparatus according to claim 1,
wherein the electrically conductive top layer is connected to an electrical circuit by which interactions with a molecule passing through the aperture can be controlled.

9. The apparatus according to claim 8,
wherein the electrical circuit is adapted to sense conductivity changes occurring when the molecule or different portions of the molecule pass through the aperture.

10. The apparatus according to claim 1,
wherein a plurality of aperture are provided.

11. The apparatus according to claim 1, wherein the aperture has a size between 2 $nm^2$ and 5 $nm^2$.

12. The apparatus according to claim 1, wherein the electrically conductive top layer comprises graphene in one monolayer.

13. The apparatus according to claim 1, wherein the bottom layer is configured in one piece and the first slit lies completely within an interior of the bottom layer.

14. The apparatus according to claim 1, wherein the material comprising the electrically conductive top layer is graphene.

15. The apparatus according to claim 1, said electrically conductive top layer further comprising a top and bottom surface, wherein the bottom surface contacts the bottom layer, and the electrical insulation is disposed on at least a part of the top surface.

16. The apparatus according to claim 1, wherein the additional layer is disposed on the top surface and the side surfaces of the electrically conductive top layer other than at the aperture.

17. A method for manufacturing an apparatus for the processing of single molecules, the apparatus comprising:

a bottom layer with a first slit;

an electrically conductive top layer with a second slit that is disposed on the bottom layer, said second slit being disposed above the first slit to provide an aperture having a dimension through which single molecules can pass therethrough, wherein the first slit is oriented oblique to the second slit;

said electrically conductive top layer comprising a material having a high electrical conductivity and further comprising an electrical insulation on at least a part of its surface;

wherein the electrically conductive top layer comprises graphene in less than five monolayers;

wherein the electrical insulation on at least a part of the surface of the electrically conductive top layer is an additional layer disposed on the electrically conductive top layer other than at the aperture;

wherein the additional layer covers a portion of edges of the top surface of the electrically conductive top layer at proximal sides of the aperture;

wherein the electrically conductive top layer is configured to have a substantially in-line surface on an entire inside wall of the aperture; and the method comprising providing a bottom layer with a first slit;

depositing an electrically conductive top layer on said bottom layer, said electrically conductive top layer comprising a material comprising graphene in less than five monolayers that has a high electrical conductivity and further includes an electrical insulation on at least a part of its surface;

producing a second slit in said top layer above the first slit to yield an aperture, wherein the first slit is oriented oblique to the second slit.

18. An apparatus for the processing of single molecules, comprising:

a bottom layer with a first slit;

an electrically conductive top layer with a second slit that is disposed on the bottom layer, said second slit being disposed above the first slit to provide an aperture having a dimension through which single molecules can pass therethrough, wherein the first slit is oriented oblique to the second slit; and said electrically conductive top layer comprising a material having a high electrical conductivity and further comprising an electrical insulation on at least a part of its surface;

wherein the electrically conductive top layer comprises a material with an electron mobility of at least 10,000 $cm^2/Vs$;

wherein the electrical insulation on at least a part of the surface of the electrically conductive top layer is an additional layer disposed on the electrically conductive top layer other than at the aperture;

wherein the additional layer covers a portion of edges of the top surface of the electrically conductive top layer at proximal sides of the aperture; and wherein the electrically conductive top layer is configured to have a substantially in-line surface on an entire inside wall of the aperture.

19. The apparatus according to claim 18, said electrically conductive top layer further comprising a top and bottom surface, wherein the bottom surface contacts the bottom layer, and the electrical insulation is disposed on at least a part of the top surface.

* * * * *